United States Patent [19]
Garber

[11] Patent Number: 5,269,802
[45] Date of Patent: Dec. 14, 1993

[54] PROSTATIC STENT

[76] Inventor: Bruce B. Garber, 400 Charles La., Wynnewood, Pa. 19096

[21] Appl. No.: 756,870

[22] Filed: Sep. 10, 1991

[51] Int. Cl.⁵ .................................................. A61M 29/00
[52] U.S. Cl. ........................................ 606/191; 623/1; 623/12; 604/8
[58] Field of Search ................. 606/191, 194, 195, 198, 606/200, 108, 153–156; 623/1, 12; 604/8, 280, 281

[56] References Cited

U.S. PATENT DOCUMENTS

| | | | |
|---|---|---|---|
| 3,657,744 | 4/1972 | Ersek | 606/153 |
| 3,908,637 | 9/1975 | Doroshow | 128/2 |
| 3,924,633 | 12/1975 | Cook et al. | 128/349 |
| 4,183,102 | 1/1980 | Guiset | 623/1 |
| 4,655,771 | 4/1987 | Wallsten | 623/1 |
| 4,762,129 | 8/1988 | Rosenbluth | 128/343 |
| 4,790,809 | 12/1988 | Kuntz | 604/8 |
| 4,820,262 | 4/1989 | Finney | 604/8 |
| 4,830,003 | 5/1989 | Wolff et al. | 128/343 |
| 4,874,360 | 10/1989 | Goldberg et al. | 604/8 |
| 4,893,623 | 1/1990 | Rosenbluth | 606/192 |
| 4,931,037 | 6/1990 | Wetterman | 604/8 |
| 4,950,227 | 8/1990 | Savin et al. | 604/8 |
| 4,950,228 | 8/1990 | Knapp, Jr. et al. | 604/8 |
| 4,955,859 | 9/1990 | Zilber | 604/8 |
| 4,957,479 | 9/1990 | Roemmer | 604/8 |
| 4,994,066 | 2/1991 | Voss | 606/108 |

OTHER PUBLICATIONS

Richard Wolf Flexible Instruments (1980).
The Prostate Book Krames Communications (undated).
Surgical Techniques in Urology Steven A. Kaplan, MD Koo, 1990 pp. 1–10.

*Primary Examiner*—C. Fred Rosenbaum
*Assistant Examiner*—William Lewis
*Attorney, Agent, or Firm*—Synnestvedt & Lechner

[57] ABSTRACT

A prostatic stent for treating benign prostatic hypertrophy (BPH) is disclosed. The stent comprises a first ring constructed of tubing; a second ring constructed of tubing; and a plurality of connecting arm members connecting said first and second rings such that the plane of said first ring is maintained substantially parallel to the plane of said second ring. In operation and use, the first ring is placed in the bladder of a patient with BPH, the second ring is placed in the prostatic urethra and the connecting arms hold back a hypertrophied prostate and prevent it from closing off the prostatic urethra.

14 Claims, 3 Drawing Sheets

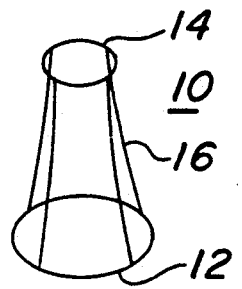
FIG. 4
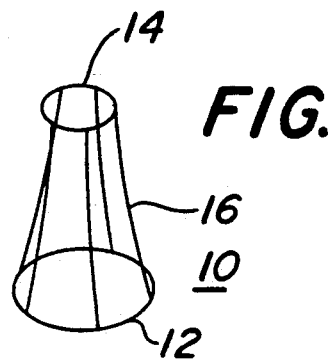
FIG. 5
FIG. 6
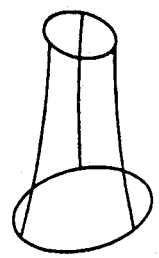
FIG. 7
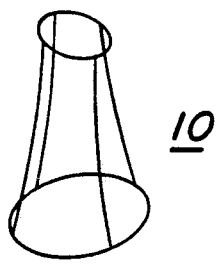
FIG. 8
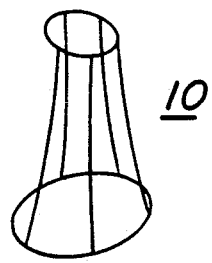
FIG. 10
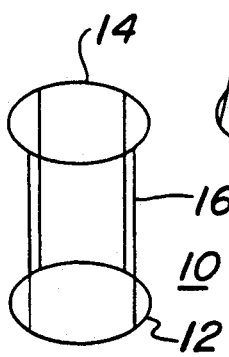
FIG. 9
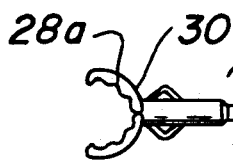

PROSTATIC STENT

FIELD OF THE INVENTION

The present invention is directed to stents, and in particular, to stents which can be used to enlarge or open a prostatic urethra blocked by an enlarged prostate, whether due to benign prostatic hypertrophy (BPH) or to prostate carcinoma.

BACKGROUND OF THE INVENTION

Benign prostatic hypertrophy (BPH) occurs in most men over the age of forty and causes clinical problems in a significant percentage of all such individuals. BPH often results in obstructive symptoms which can lead to bladder decompensation that may culminate in urinary retention. Elderly or debilitated patients with BPH often have multiple medical problems which may preclude surgical removal of the bladder outlet obstruction as a viable option. Currently, these patients often require long-term indwelling bladder catheterization, which may lead to multiple problems, including urinary tract infection and sepsis, epididymitis, bladder stones and bladder cancer.

The surgical treatment of BPH has been routine for many years. One method of surgical treatment is open prostatectomy whereby an incision is made to expose the enlarged prostate gland. The hypertrophied tissue is removed under direct vision. Another method, which has gained increasing usage in recent years, is transurethral resection. In this procedure, an instrument called a resectoscope is placed into the external opening of the urethra and an electrosurgical loop is used to carve away sections of the prostate gland from within the prostatic urethra under endoscopic vision. See *Benign Prostatic Hypertrophy*, edited by Frank Hinman, M.D. and particularly the chapter entitled "Prostatectomy, Past and Present" by Geoffrey D. Chisholm, M.D.

Notwithstanding the significant improvement in patient care resulting from the widespread application of transurethral resection, there remains a need for less invasive methods of treating the symptoms of prostatic enlargement. Various complications including impotence, incontinence, bleeding, infection, residual urethral obstruction, urethral stricture, and retrograde ejaculation may affect the patient following transurethral resection.

One of the earliest applied methods of relieving the acute urinary retention symptomatic of prostate enlargement was the placement of a catheter through the external urethral opening into the bladder thereby allowing the outflow of urine from the bladder by way of the catheter lumen. Such urinary catheters typically employ a balloon at the tip which, when inflated, prevents the expulsion of the catheter from the body. Although this method is effective in achieving urinary outflow, it is generally unacceptable as a long term treatment due to problems of infection and interference with sexual activity. In addition, such patents require close monitoring and frequent catheter changes. This results in great inconvenience to the patient and high medical costs.

The use of dilating bougies and sounds for mechanical dilation of the prostatic urethra have been attempted without success in the treatment of BPH. The fibrous and muscular tissue of the prostate gland rebounds after dilation, resulting in only a temporary reduction of urethral constriction.

A method of treating prostate disease involving the application of balloon dilation in a similar manner as in percutaneous transluminal angioplasty of arterial occlusions has been proposed in an article in the September 1984 issue of *Radiology*, page 655 entitled "Prostatic Hyperplasia: Radiological Intervention" by H. Joachim Burhenne, M.D., et al. This method of prostate dilation can be expected to have only a short term alleviation of urinary retention as the fibrous and resilient hypertrophied prostate gland will in a relatively short period of time cause the constriction of the prostatic urethra to recur. Also in the angioplasty arts, Palmaz, et al. have described the percutaneous, sheathed insertion of an expandable endoprosthesis into various major arteries of dogs in the article "Expandable Intraluminal Graft: A Preliminary Study" in the July 1985 issue of Radiology at page 73.

Finally, over the past decade, various alternative surgical and non-surgical therapeutic treatments for BPH have been developed. These include medical therapy (anti-androgens, alpha-blockers, 5-alpha reductase inhibitors), ultrasonic aspiration of the prostate, transurethral incision, cryosurgery and hyperthermia.

A most promising alternative in the treatment of BPH has been the introduction and use of prostatic stents. A prostatic stent or spiral was first described by K. W. Fabian in *Urologe* (1980). There have been many subsequent develoments including the Prostakath ® (developed by Engineers and Doctors A/S, Copenhagen, Denmark). This stent, which is a helical coil or spiral composed of stainless steel, is coated with 24 karat gold, which aids in preventing encrustation. The straight portion remains in the prostatic urethra while the distal portion remains in the bulbar urethra.

Another currently available stent is the UroLume Wallstent manufactured by American Medical Systems. This stent is constructed from a biomedical super alloy prosthesis woven in a tubular mesh and produced in various diameters and lengths. This stent is preloaded in a delivery system that allows direct visualization with the prosthesis and the urethra throughout the entire insertion procedure.

A number of patents directed to prostatic stents have also issued. U.S. Pat. No. 4,893,623 discloses a tubular stent having a plurality of passages comprising a first plurality of parallel filaments which are aligned at a diagonal to a second plurality of parallel filaments. The stent disclosed in U.S. Pat. No. 4,893,623 is formed from a single piece of material, such as a malleable biological compatible metal, and is designed to hold its expanded configuration under stress exerted by a hypertrophied prostate gland. See also U.S. Pat. No. 4,762,128. The stent disclosed in this patent is similar to the Urolume Wallstent. See "Prostatic Stents", *Current Surgical Techniques in Urology*, Kaplan and Koo (1990).

U.S. Pat. No. 4,994,066 also discloses a stent for treating BPH. The stent has a cylindrical conduit having a conical flange on one end and an annular flange on the other. The stent is constructed of a medical grade elastomer which is compressed for implantation and can thereafter be left for extended periods of time.

Finally, U.S. Pat. No. 4,955,859 discloses a high-friction prostatic stent. The stent includes a textured fabric layer for frictionally engaging the urethral walls to anchor the device within the prostatic urethra and to prevent migration back into the bladder or down the urethra.

Each of these stents have several problems associated therewith. Initially, stents such as disclosed in U.S. Pat. Nos. 4,893,623 and 4,955,859 can dig into surrounding tissue of the prostate, thereby leading to discomfort, inflammation and infection. As the stent of U.S. Pat. No. 4,893,623 expands, the perforations become larger and greater pressure is exerted between the expanded stent and the enlarged prostate. Under such conditions, the tissue of the urethral walls attempts to penetrate even more deeply into the perforations of the stent and thereby render the stent difficult, if not impossible, to remove without major surgery. Further, stents such as disclosed in U.S. Pat. No. 4,893,623 must be inserted using complex and specialized apparatus.

The Prostakath ®, identified above, has not gained widespread acceptance, because of concerns regarding encrustation of the metal spiral which may cause the spiral to adhere to the urethral walls, thereby necessitating surgery to remove the device. There have been further reservations that the tip of the spring may cause bladder irritation, and further concerns that attempts to remove the metal spiral by endoscopically pulling on its distal end may cause the spiral to unwind such that the sharp end of the wire lacerates the urethra. Finally, this stent has also experienced migration and may cause incontinence.

In addition, some prior art stents have typically lacked sufficient flexibility and may be difficult to use with patients having unusual or abnormally shaped prostatic lobes. Some prior art stents have also been expensive to fabricate.

It would be desirable to provide a prostatic stent which can accommodate prostates having different lengths, widths and shapes. Such a stent could be constructed from a tubing material of the type long successfully utilized in ureteral stents and catheters.

It would be further desirable to have a prostatic urethral stent which would not become incorporated into the tissues of the prostate, as is characterized by wire-mesh stents.

It is thus an object of the present invention to provide a novel prostatic stent constructed from tubing of the type used in ureteral stents and catheters and which improves over prior art prostatic stents.

It is still a further object of the present invention to provide a prostatic stent which will not become easily dislodged or migrate.

It is yet a further object of the present invention to provide a prostatic stent which can be easily inserted and removed without open surgical intervention.

It is still yet an additional object of the present invention to provide a prostatic stent which is less irritating to the urethra and does not interfere with urinary continence.

These and other objects of the present invention will become apparent from the summary and detailed description which follow.

SUMMARY OF THE INVENTION

In accordance with the present invention, a novel prostatic stent is disclosed. The stent comprises a first ring constructed of a polymeric tubing, a second ring constructed of a polymeric tubing, and a plurality of branching members connecting said first and second ring such that the plane of said first ring is maintained substantially parallel to the plane of said second ring. In use the stent is positioned in the prostatic urethra. The first ring is placed inside the bladder neck. The second ring is placed in the distal prostatic urethra. The branching arms function to maintain open a urethra closed or blocked by a hypertrophied prostate. In use, the pressure of the bladder neck against the branching arms tends to arc the arms inward, tending to wedge the stent in place, thus preventing stent migration. By varying the numbers and lengths of the branching arms and the size of the rings, the stent of the present invention can accommodate patients having different shaped and sized prostates.

BRIEF DESCRIPTION OF THE FIGURES

FIGS. 4 and 5 are elevated perspective views of prostatic stents which can be utilized for prostates having larger amounts of lateral lobe and anterior tissue.

FIGS. 6-8 illustrate prostatic stents in accordance with the present invention specifically suitable for prostates having median lobe enlargement in which the two tubing rings are not parallel.

FIG. 9 is an insertion mechanism for inserting the stent of the present invention through standard cystoscopic equipment.

FIG. 10 is an elevated view of a stent in accordance with the present invention having rings of equal sized diameters.

DETAILED DESCRIPTION OF THE PREFERRED EMBODIMENT

Figure 1:
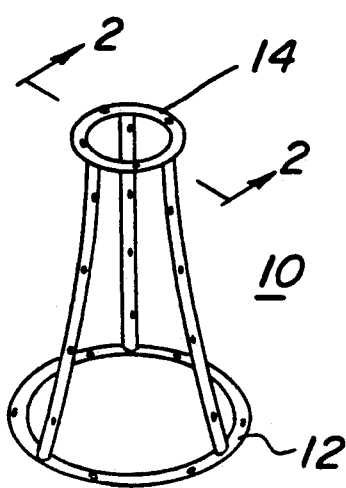
FIG. 1 is an elevated perspective view of the prostatic stent of the preferred embodiment.
Figure 2:
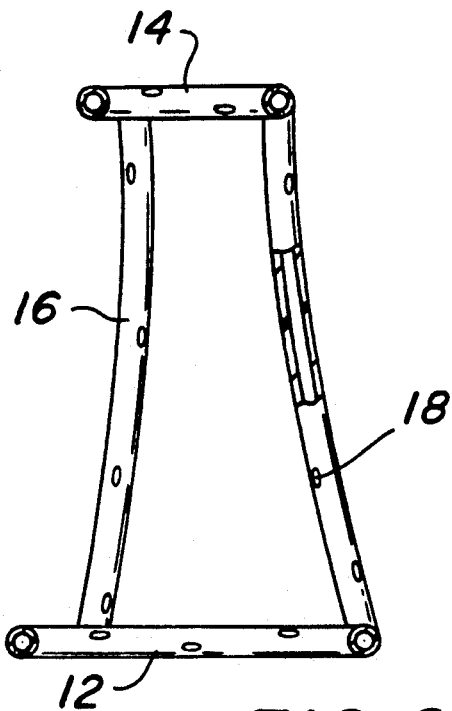
FIG. 2 is a partial section view of the prostatic stent of the preferred embodiment along line 2—2 a FIG. 1.

The present invention is described with reference to the enclosed Figures wherein the same numbers are utilized where applicable. Referring to FIGS. 1 and 2, the stent 10 of the present invention comprises a first ring 12 coupled to a second ring 14. As shown, the diameter of the first ring 12 is larger than that of the second ring 14. The first ring 12 and second ring 14, are joined together by a plurality of connecting arms 16. The connecting arms 16 are connected to the rings 12, 14 so as to maintain the rings 12, 14 in a substantially co-planar or parallel relationship.

The rings 12, 14 and connecting arms or members 16 are preferably constructed of elongated polymeric tubular members of uniform outside diameter. The connecting members 16 and rings 12, 14 may be constructed from a variety of materials which are biocompatable and have desired physical properties. An example of a suitable material is a Teflon ® material marketed by Dupont under the trademark Silitek ®. Materials of this type have heretofore been successfully utilized in ureteral stents such as disclosed in U.S. Pat. Nos. 4,931,0371, 4,950,228; 4,790,8809; and 4,820,262. This tubing may be referred to as "J" or "double-J" type tubing. Tubing of this type further combines longitudinal rigidity with the softness necessary for comfort. This material also possesses good memory characteristics. As seen in FIG. 2, the rings 12, 14 and connecting member 16 are preferably hollow and include holes or apertures 18. The holes 18 provide for fluid communication and facilitate urinary continence. While the present invention has been described in the context of tubing having holes or apertures, it is to be appreciated by those skilled in the art that the rings 12, 14 and connecting arms 16 can be constructed from a non-hollow polymeric material which does not include holes or apertures.

The stent 10 also preferably should be doped with a radiopaque compound or material to permit visualization by X-ray. Alternatively, the stent may be doped with a radiopaque strip. Barium sulfate is known to be an acceptable radiopaque agent and may be utilized with the stent 10 of the present invention. Further, to provide sufficient rigidity so as to prevent collapsing, the rings 12 and 14 and connecting arms 16 should be fabricated from a material having a durometer of about 40 on the Shore "D" scale.

Figure 3:
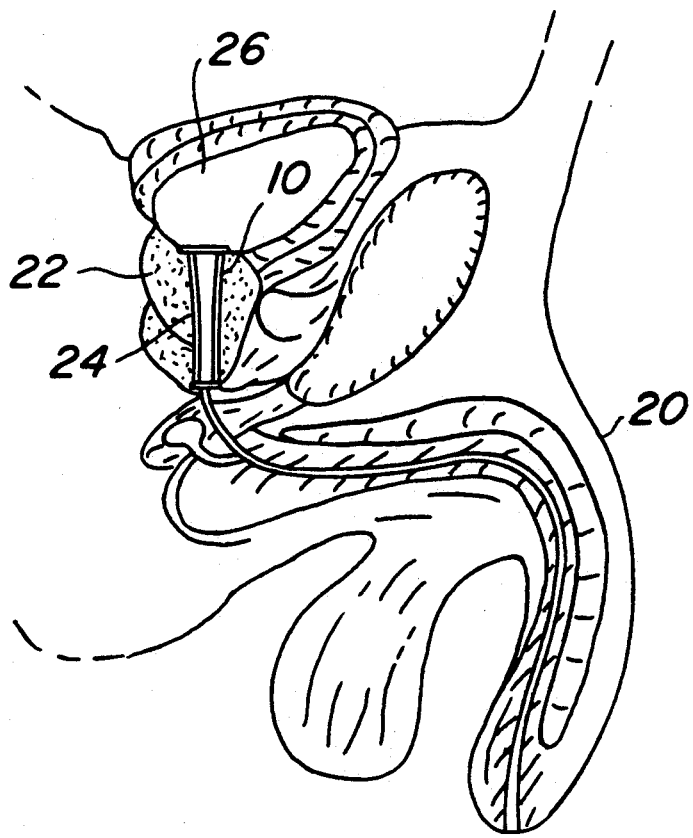
FIG. 3 illustrates the implantation of the prostatic stent of the preferred embodiment within the prostatic urethra.

FIG. 3 illustrates the male reproductive organs 20, prostate gland 22, prostatic urethra 24, bladder 26 and stent 10 of the present invention. As inserted, the large ring 12 of the stent is positioned inside the bladder neck. The smaller ring is positioned in the distal prostatic urethra 24. For some patients, the larger ring will extend further into the bladder 26 and the smaller ring will extend into the prostatic urethra. The connecting arms 16 restrain the hypertrophied prostate and maintain the urethra 24 in an open position. As can be seen, as the prostate 22 tends to close against the connecting arms 16, the arms arc inward. The stent 10 assumes an hour glass shape which tends to wedge it in place with respect to the prostate gland.

Referring to FIGS. 4-8, various stents produced in accordance with the present invention are shown. As shown, each of the stents have two substantially circular rings 12, 14 connected by multiple flexible arms of tubing 16. The stents may be constructed from the polymeric materials discussed above. The number and lengths of connecting arms 16 may be varied according to the particular needs of the patient. Because prostates come in many different lengths and shapes, a family of stents could be constructed to accommodate different anatomical configurations. Prostates having larger amounts of lateral lobe and anterior tissue might require a stent having four or five arms 16 to hold the prostatic urethra open, such as shown in FIG. 4 and 5. Another typical anatomical variant includes prostatic median lobe enlargement. For this type of prostate, connecting arms 16, having different lengths, create a non-parallel ring structure such as shown in FIGS. 6-8. Further, it is anticipated that each of the stents 10 could be made with longer or shorter branching arms 16 to accommodate longer or shorter prostatic urethras.

Figure 9A:
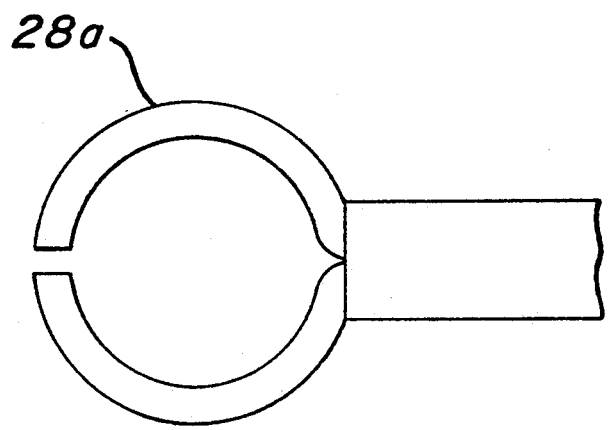
FIGS. 9a and 9b illustrate the forceps of the insertion mechanism of the present invention in an open and closed position.
Figure 9B:
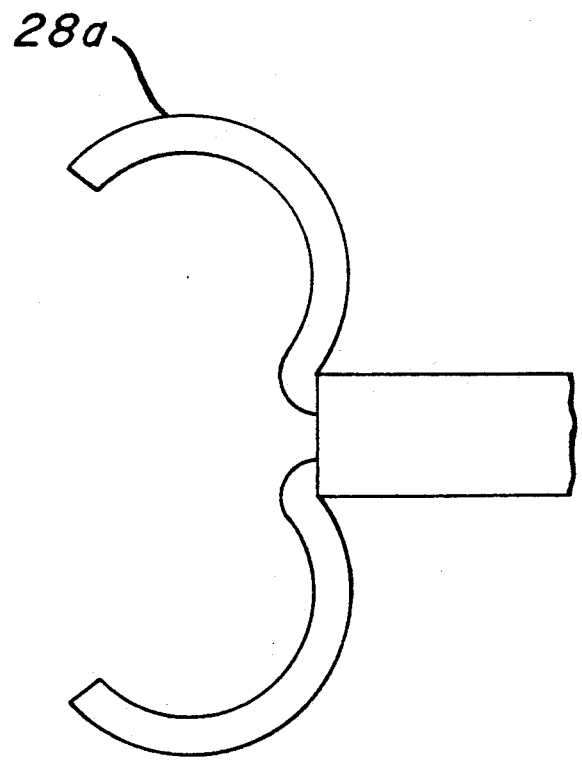

Referring to FIG. 9, an insertion mechanism 28 for use in inserting the stent 10 is shown. The instrument comprises a modified flexible cystoscopic grasping forceps, similar in design to those manufactured by the Richard Wolfe Company of Rosemont, Ill. In use, the mechanism 28 is inserted into the penis of the patient through a cystoscope, and the stent 10 is grasped by the forceps 28a and pushed into the bladder 26. The forcep jaws 28a are then used to grab the small ring 14 and position the stent 10 in the urethra as shown in FIG. 3.

While the present invention has been described with reference to the enclosed Figures, it is to be appreciated that other embodiments are envisioned by the present invention and that the true nature and scope of the present invention should be determined with reference to the claims appended hereto. Specifically, while the present invention has been described in the context of an embodiment having a two substantially circular rings, it is to be appreciated that the stent of the present invention may contain more than two rings and that the rings may be oval or elliptical. Further, as shown in FIG. 10, stents in accordance with the present invention, may have rings 12, 14 of equal diameter.

I claim:

1. A prostatic stent comprising:
   a first ring having a first diameter and constructed from a polymeric material for placement in the prostatic urethra of a patient;
   a second ring having a second diameter larger than said first diameter constructed from a polymeric material for placement in the bladder of a patient;
   a plurality of arm members constructed from a polymeric material for connecting said first and second rings, said arm members functioning to prevent an enlarged prostate gland from closing off the prostatic urethra;

2. The prostatic stent of claim 1 wherein said arm members connect said first and second rings such that the plane of said first ring is maintained substantially parallel to the plane of said second ring.

3. A prostatic stent comprising:
   a first ring constructed from a tubing for placement in the bladder of a patient having benign prostatic hypertrophy;
   a second ring constructed from a tubing for placement in the prostatic urethra of a patient having benign prostatic hypertrophy, said first ring having a larger diameter than said second ring, a plurality of arm members connecting said first and second ring such that the plane of said first ring is maintained substantially parallel to the plane of said second ring, said arm members functioning to prevent an enlarged prostate gland from closing off the prostatic urethra.

4. The prostatic stent of claim 3 wherein said first ring, second ring and plurality of arms are constructed from a hollow polymeric tubing.

5. The prostatic stent of claim 3 wherein said prostatic stent contains a radiopaque doping agent or marking material.

6. A prostatic stent comprising:
   a first ring having a first larger diameter, said first ring being constructed from a tubing for insertion into the bladder of a patient; and
   a second ring having a second diameter, said second diameter being smaller than said first diameter, said second ring being constructed from a tubing for insertion in the prostatic urethra of a patient; and
   a plurality of flexible arms joining said first and second rings so as to maintain said rings in a substantially coplanar relationship, said flexible arms functioning to maintain an enlarged prostate in an open position.

7. The prostatic stent of claim 6 wherein said stent contains at least three flexible arms.

8. The prostatic stent of claim 6 wherein said stent contains at least four flexible arms.

9. The prostatic stent of claim 6 wherein said stent contains at least five flexible arms.

10. The prostatic stent of claim 6 wherein said stent contains at least six flexible arms.

11. The prostatic stent of claim 6 wherein said plurality of flexible arm are constructed from a hollow polymeric tubing.

12. A prostatic stent comprising:
- a first ring constructed from a hollow tubing having a first diameter for insertion into the bladder of a patient;
- a second ring constructed from a hollow tubing and having a second diameter not equal to said first diameter for insertion into the prostatic urethra of a patient; and
- a plurality of connecting branches connecting said first and second rings, said first ring, second ring and branching arms being doped with a radiopaque agent.

13. The prostatic stent of claim 12 wherein said plurality of connecting branches have different lengths.

14. The prostatic stent of claim 12 wherein radiopaque agent is barium sulfate.

* * * * *